US00PP31095P2

(12) United States Plant Patent
O'Connell

(10) Patent No.: US PP31,095 P2
(45) Date of Patent: Nov. 19, 2019

(54) ***ECHEVERIA* PLANT NAMED 'LOVE'S FIRE'**

(50) Latin Name: *Echeveria agavoides*
Varietal Denomination: Love's Fire

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 16/350,546

(22) Filed: Nov. 30, 2018

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Echeveria agavoides* cultivar named 'Love's Fire' is disclosed, rapid, robust growth and improved resistance to fungal disease brought on by over-watering. Plants offset freely, producing an attractive cluster. Foliage is bright red during cooler months and distinctively red during the rest of the year. *Echeveria* is a popular genus, typically produced as container plants for the patio or as landscape plants.

1 Drawing Sheet

Latin name of the genus and species: *Echeveria agavoides.*

Variety denomination: 'LOVE'S FIRE'.

BACKGROUND OF THE INVENTION

The new cultivar, *Echeveria* 'Love's Fire', is the product of a planned breeding program. The new variety originated from a self-pollination of the parent, a proprietary, unpatented *Echeveria agavoides* cultivar known as *Echeveria agavoides* 'Rubra' hybrid "A". The self-pollination was made during March 2013, in Vista, Calif., at a commercial greenhouse. The new cultivar 'Love's Fire' was selected by the inventor, Renee O' Connell, in February 2014, in Vista, Calif. at a commercial greenhouse.

Asexual reproduction of the new cultivar 'Love's Fire' was first performed in Vista, Calif., at a commercial greenhouse, by vegetative offsets in September 2015. *Echeveria* 'Love's Fire' has since produced at least 7 generations and has shown that the unique features of this cultivar are stable and reproduced true to type.

SUMMARY OF THE INVENTION

The cultivar 'Love's Fire' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LOVE'S FIRE'. These characteristics in combination distinguish 'LOVE'S FIRE' as a new and distinct *Echeveria* cultivar:

1. *Echeveria* 'Love's Fire' is faster growing than many *Echeveria agavoides* cultivars, enhancing production times in the commercial nursery environment.

2. *Echeveria* 'Love's Fire' grows more robustly than many other *Echeveria agavoides* cultivars, displaying a resistance to the fungal diseases common with over-watering *Echeveria agavoides.*
3. *Echeveria* 'Love's Fire' displays upswept rosettes of longer, more slender leaves as compared to many other *Echeveria agavoides* cultivars.
4 *Echeveria* 'Love's Fire' freely produces offsets, creating an aesthetically attractive cluster in an 8" pot, unlike many other *Echeveria agavoides* cultivars.
5. The freely produced offsets of *Echeveria* 'Love's Fire' enhance rapid propagation of the variety in the commercial nursery environment.
6. The rosette of *Echeveria* 'Love's Fire' blushes fire red during the cooler months, but retains much of this red coloration nearly year-round. Drought, bright light or cool temperatures intensify red blush.

PARENTAL COMPARISON

Plants of the new cultivar 'Love's Fire' are similar to plants of the parent in most horticultural characteristics. However, plants of the new cultivar 'Love's Fire' differ in the following:

1. *Echeveria* 'Love's Fire' exhibits faster growth than does *Echeveria agavoides* 'Rubra' hybrid "A".
2. *Echeveria* 'Love's Fire' produces a more enhanced red coloration, as compared with *Echeveria agavoides* 'Rubra' hybrid "A".
3. *Echeveria* 'Love's Fire' produces larger rosettes than *Echeveria agavoides* 'Rubra' hybrid "A".
4. *Echeveria* 'Love's Fire' freely produces offsets, whereas *Echeveria agavoides* 'Rubra' hybrid "A" is sparsely offsetting.
5. *Echeveria* 'Love's Fire' produces slightly more slender leaves than *Echeveria agavoides* 'Rubra' hybrid "A".

COMMERCIAL COMPARISON

The new cultivar 'Love's Fire' can be compared to the unpatented commercial variety *Echeveria agavoides* 'Romeo'. Plants of the new cultivar 'Love's Fire' differ in the following:

1. *Echeveria* 'Love's Fire' produces longer, more slender leaves than does *Echeveria agavoides* 'Romeo'.
2. *Echeveria* 'Love's Fire' displays much more resistance to fungal and bacterial rot than does *Echeveria agavoides* 'Romeo'.
3. *Echeveria* 'Love's Fire' offsets more freely at a smaller pot size than does *Echeveria agavoides* 'Romeo'.
4. The rosette of *Echeveria* 'Love's Fire' displays a more upswept morphology than does the rosette of *Echeveria agavoides* 'Romeo', which tends to be flatter in morphology.

The new cultivar 'Love's Fire' can be compared to the unpatented *Echeveria agavoides* 'Red Edge'. Plants of the new cultivar 'Love's Fire' are similar to *Echeveria agavoides* 'Red Edge' in most horticultural characteristics. However, plants of the new cultivar 'Love's Fire' differ in the following:

1. The rosette of *Echeveria* 'Love's Fire' blushes fire red in totality, whereas the rosette of *Echeveria agavoides* 'Red Edge' exhibits the red coloration on the leaf apices and margins.
2. *Echeveria* 'Love's Fire' displays rosettes with longer, slender leaves, whereas *Echeveria agavoides* 'Red Edge' exhibits flatter, wider, shorter leaves.
3. *Echeveria* 'Love's Fire' exhibits faster growth than *Echeveria agavoides* 'Red Edge', enhancing production times in a commercial nursery.
4. The rosette of *Echeveria* 'Love's Fire' displays a more upswept morphology, whereas the rosette of *Echeveria agavoides* 'Red Edge' is flatter in morphology.

BRIEF DESCRIPTION OF THE PHOTOGRAPH

The accompanying photograph illustrates in full color typical plants of 'LOVE'S FIRE' grown in a greenhouse in Vista, Calif. The plant is approximately 10 months age and grown under approximately 3000-foot candles of light in a greenhouse in Vista, Calif.. No artificial light, photoperiodic treatments or chemical treatments were given to the plants. The photograph was taken using conventional techniques and equipment. While the colors in the photograph may display variances of color as compared to the living cultivar, due to LRV (light reflectance value), they are as accurate as possible using conventional photographic techniques. Colors in the photograph may appear to differ slightly from the color values cited in the botanical description, which accurately describe the colors of the new *Echeveria* plant. Temperatures ranged from approximately 2° C. to 38° C. night and day.

DETAILED BOTANICAL DESCRIPTION

In the following description, color references are made to The Royal Horticultural Society Colour Chart, 2007, except where general terms of ordinary dictionary significance are used. The following observations and measurements describe 'Love's Fire' plants in a commercial greenhouse in Vista, Calif. Temperatures ranged from 2° C. to 38° C. night and day. No artificial light, photoperiodic treatments or chemical treatments were given to the plants. Natural light conditions were approximately 2500 to 2500 fc of light. Measurements and numerical values represent averages of typical plant types.

Botanical classification: *Echeveria agavoides* 'LOVE'S FIRE'.

PROPAGATION

Type of propagation typically used: Terminal vegetative cuttings.

Time to initiate roots: About 11 days at approximately 24° C.

Root description: Fibrous.

PLANT

Age of plant described: Approximately 4 months from a cutting.

Container size of the plant described: 10 cm.

Growth habit: Moderately dense, symmetrical rosette.

Height: Approximately 6 to 8 cm to top of highest leaf.

Plant spread: Approximately 12 to 14 cm.

Growth rate: Moderate to rapid.

Branching characteristics: Rosette forming, no branching.

FOLIAGE

Leaf:

*Arrangement*.—Rosulate.

*Average length*.—Average 5.5 cm.

*Average width*.—2.0 cm.

*Thickness*.—5 to 10 mm.

*Shape of blade*.—Deltate.

*Apex*.—Acute. Slightly sharp.

*Base*.—Truncate.

*Margin*.—Entire.

*Aspect*.—Moderately concave.

*Texture of top surface*.—Glabrous.

*Texture of bottom surface*.—Glabrous.

*Appearance of top surface*.—Matte, somewhat of a glow from the intensity of the color, but, not iridescent.

*Appearance of bottom surface*.—Matte to nearly shiny.

*Quantity of leaves per plant*.—Average range 25 to 32.

*Color*.—Young foliage upper side, towards apex: Near RHS Greyed-Purple 187A, and 185A, margin brightly colored near Red 53A. Young foliage upper side, mid-section: Near RHS Greyed-Green 191A heavily flushed Greyed-Purple 187A, margin brightly colored Red 53A. Young foliage upper side, towards base of leaf: Base near Green 137D. Young foliage, under side, towards apex of leaf: Near RHS Greyed-Purple 185A. Young foliage upper side, mid-section: Near RHS Greyed-Purple 185A. Some marbling near Greyed-Green 191A, margin brightly colored Red 53A. Young foliage, under side, towards base of leaf: Near RHS Green 138B. Mature foliage upper side, towards apex of leaf: Near RHS Greyed-Green 191A completely covered in Greyed-Purple 185A, margin brightly colored Red 53A. Mature foliage upper side mid-section: Near RHS Greyed-Green 191A. heavily flushed Greyed-Purple 185A, margin brightly colored Red 53A. Mature foliage, upper side, towards base of leaf: Near RHS Green 138C. Mature foliage, under side, towards apex of leaf: Near Greyed-Purple 185A. Margin near Red 53A. Mature foliage under side mid-section: Near Green 138A heavily flushed 185B and 185C. Margin near Red 53A. Mature foliage, under side, towards base of leaf: Near RHS Greyed-Purple 185B, fading to 185C towards center. Center section near Greyed-Green 194B. Margin near Greyed-Purple 185B.

*Venation*.—There is no visual appearance of venation.

FLOWER

None observed to date.

REPRODUCTIVE ORGANS

None observed to date.

OTHER CHARACTERISTICS

Fruits and seeds: Not observed.

Temperature tolerance: Tolerates temperatures from approximately −2° C. to at least 35° C.

Disease/pest resistance: Resistance observed to fungal diseases common with overwatering of *Echeveria* plants. Neither resistance or susceptibility to other normal diseases and pests of *Echeveria* has been observed.

Drought tolerance: Tolerates at least 3 weeks of high temperatures without supplemental water, showing no serious damage to plant.

What is claimed is:

1. A new and distinct cultivar of *Echeveria* plant named 'LOVE'S FIRE' as herein illustrated and described.

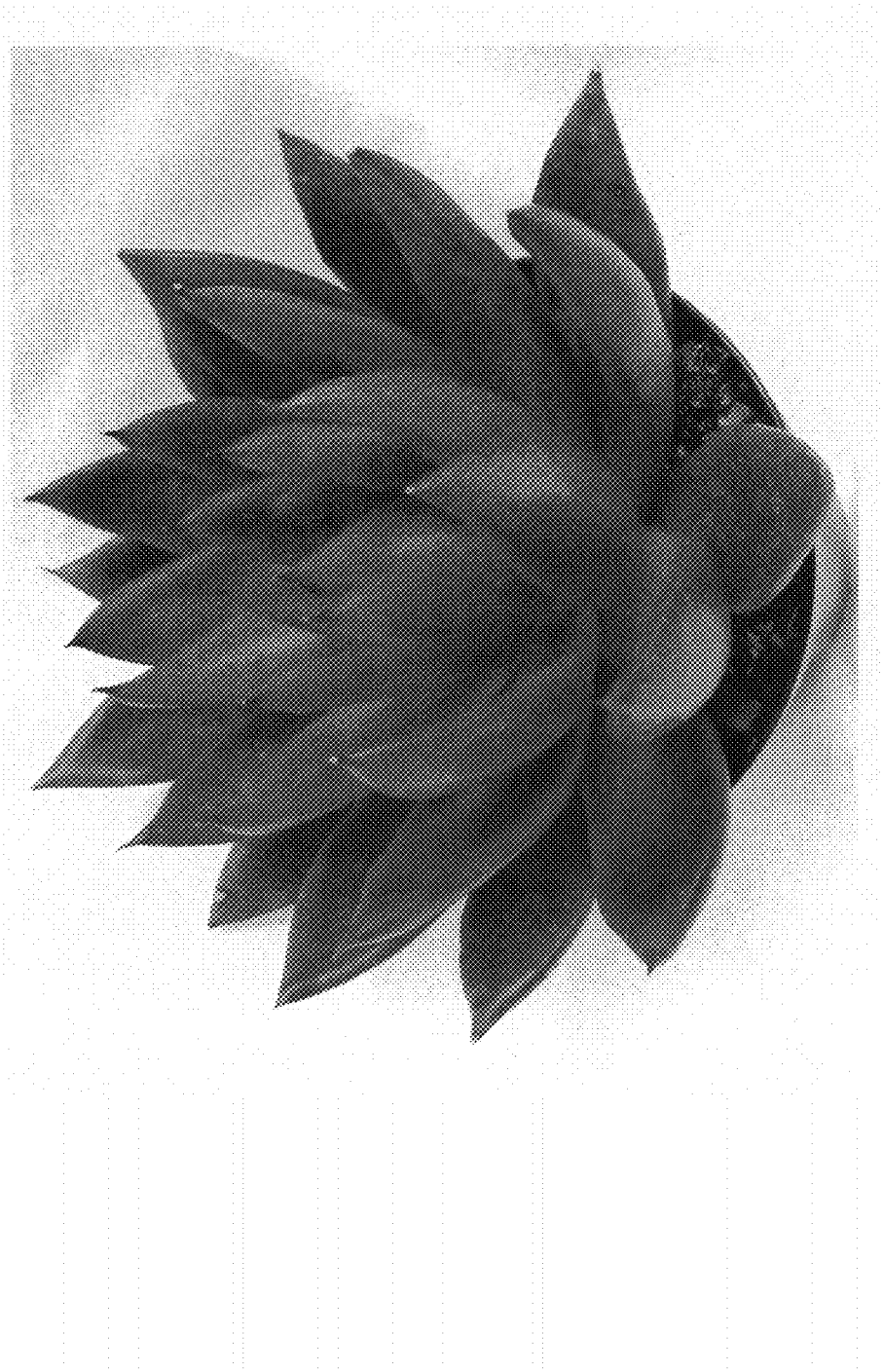

* * * * *